US008685714B2

(12) United States Patent
Hodges et al.

(10) Patent No.: US 8,685,714 B2
(45) Date of Patent: Apr. 1, 2014

(54) IMMUNOSENSOR

(75) Inventors: Alastair Hodges, San Diego, CA (US); Ron Chatelier, San Diego, CA (US)

(73) Assignee: Universal Biosensors Pty Ltd, Rowville (AU)

( * ) Notice: Subject to any disclaimer, the term of this patent is extended or adjusted under 35 U.S.C. 154(b) by 0 days.

(21) Appl. No.: 10/830,841

(22) Filed: Apr. 22, 2004

(65) Prior Publication Data

US 2004/0203137 A1  Oct. 14, 2004

Related U.S. Application Data

(63) Continuation of application No. 09/616,433, filed on Jul. 14, 2000, now abandoned.

(51) Int. Cl.
*C12M 1/34* (2006.01)

(52) U.S. Cl.
USPC ........ 435/288.5; 422/947; 435/7.93; 436/809

(58) Field of Classification Search
USPC .................. 435/4, 7.1, 7.92, 174–177, 287.1, 435/287.2, 288.5, 288.7, 808, 7.91, 14, 190, 435/19, 2, 288.4, 966, 7.93; 436/518–528, 436/164, 172, 805, 806, 904, 809; 422/68.1, 82.01, 82.05, 947
See application file for complete search history.

(56) References Cited

U.S. PATENT DOCUMENTS

| | | |
|---|---|---|
| 3,552,928 A | 1/1971 | Fetter |
| 4,053,381 A | 10/1977 | Hamblen et al. |
| 4,076,596 A | 2/1978 | Connery et al. |
| 4,125,372 A | 11/1978 | Kawai et al. |
| 4,168,146 A | 9/1979 | Grubb et al. |
| 4,224,125 A | 9/1980 | Nakamura et al. |
| 4,225,557 A | 9/1980 | Hartl et al. |
| 4,298,011 A | 11/1981 | Mangurten et al. |
| 4,301,412 A | 11/1981 | Hill et al. |
| 4,301,414 A | 11/1981 | Hill et al. |
| 4,316,801 A * | 2/1982 | Cooper ........................... 210/90 |
| 4,319,969 A | 3/1982 | Oda et al. |
| 4,323,536 A * | 4/1982 | Columbus ........................ 422/56 |
| 4,374,013 A | 2/1983 | Enfors |
| 4,376,825 A | 3/1983 | Rubenstein et al. |
| 4,404,066 A | 9/1983 | Johnson |
| 4,426,251 A | 1/1984 | Ida et al. |

(Continued)

FOREIGN PATENT DOCUMENTS

| | | |
|---|---|---|
| AU | 31042/93 | 7/1993 |
| AU | 54873/94 | 8/1994 |

(Continued)

OTHER PUBLICATIONS

Electrode. Gibilisco, S. Illustrated dictionary of electronics, McGraw-Hill Professional, 8d. (2001). p. 237.*

(Continued)

*Primary Examiner* — Melanie Y Brown
*Assistant Examiner* — Erik B Crawford
(74) *Attorney, Agent, or Firm* — Davis Wright Tremaine LLP

(57) ABSTRACT

This invention describes a quantitative, inexpensive, disposable immunosensor that requires no wash steps and thus generates no liquid waste. Moreover, in preferred embodiments of the sensor no timing steps are required of the user, and the sensor can be readily adapted to antigen-antibody interactions over a wide kinetic range.

28 Claims, 2 Drawing Sheets

(56) References Cited

U.S. PATENT DOCUMENTS

| | | | |
|---|---|---|---|
| 4,431,004 A | 2/1984 | Bessman et al. | |
| 4,431,507 A | 2/1984 | Nankai et al. | |
| 4,434,236 A | 2/1984 | Freytag | |
| 4,446,232 A | 5/1984 | Liotta | |
| 4,468,469 A | 8/1984 | Atkinson et al. | |
| 4,508,613 A | 4/1985 | Busta et al. | |
| 4,508,821 A | 4/1985 | Mansour et al. | |
| 4,517,287 A | 5/1985 | Scheibe et al. | |
| 4,517,291 A | 5/1985 | Seago | |
| 4,533,440 A | 8/1985 | Kim | |
| 4,545,382 A | 10/1985 | Higgins et al. | |
| 4,552,840 A | 11/1985 | Riffer | |
| 4,604,264 A | 8/1986 | Rothie et al. | |
| 4,637,978 A | 1/1987 | Dappen | |
| 4,654,197 A | 3/1987 | Lilja et al. | |
| 4,696,748 A | 9/1987 | Nitadori et al. | |
| 4,708,929 A * | 11/1987 | Henderson | 435/7.5 |
| 4,711,245 A | 12/1987 | Higgins et al. | |
| 4,758,323 A * | 7/1988 | Davis et al. | 204/403.14 |
| 4,790,979 A | 12/1988 | Terminiello et al. | |
| 4,797,256 A | 1/1989 | Watlington, IV | |
| 4,820,489 A | 4/1989 | Rothe et al. | |
| 4,859,583 A | 8/1989 | Heller et al. | |
| 4,871,258 A | 10/1989 | Herpichboehm et al. | |
| 4,883,764 A | 11/1989 | Kloepfer | |
| 4,897,173 A | 1/1990 | Nankai et al. | |
| 4,900,424 A | 2/1990 | Birth et al. | |
| 4,919,770 A | 4/1990 | Preidel et al. | |
| 4,943,522 A | 7/1990 | Eisinger et al. | |
| 4,943,533 A | 7/1990 | Mendelsohn et al. | |
| 4,960,415 A | 10/1990 | Reinmuller | |
| 4,963,498 A | 10/1990 | Hillman et al. | |
| 4,963,815 A | 10/1990 | Hafeman | |
| 4,988,429 A | 1/1991 | Matthiessen | |
| 4,994,238 A | 2/1991 | Daffern et al. | |
| 5,004,685 A * | 4/1991 | Arai et al. | 435/25 |
| 5,059,908 A | 10/1991 | Mina | |
| 5,077,017 A * | 12/1991 | Gorin et al. | 422/100 |
| 5,096,809 A | 3/1992 | Chen et al. | |
| 5,098,841 A * | 3/1992 | Ghisalba et al. | 435/280 |
| 5,116,576 A * | 5/1992 | Stanley | 422/55 |
| 5,120,420 A | 6/1992 | Nankai et al. | |
| 5,122,244 A | 6/1992 | Hoenes et al. | |
| 5,126,034 A | 6/1992 | Carter et al. | |
| 5,128,015 A | 7/1992 | Szuminsky et al. | |
| 5,141,868 A | 8/1992 | Shanks et al. | |
| 5,156,972 A | 10/1992 | Issachar | |
| 5,179,005 A | 1/1993 | Phillips et al. | |
| 5,183,740 A | 2/1993 | Ligler et al. | |
| 5,185,256 A | 2/1993 | Nankai et al. | |
| 5,192,415 A | 3/1993 | Yoshioka et al. | |
| 5,229,282 A | 7/1993 | Yoshioka et al. | |
| 5,230,866 A * | 7/1993 | Shartle et al. | 422/68.1 |
| 5,268,890 A | 12/1993 | Colescott | |
| 5,272,087 A | 12/1993 | El Murr et al. | |
| 5,272,258 A | 12/1993 | Siegel et al. | |
| 5,306,623 A | 4/1994 | Kiser et al. | |
| 5,312,590 A | 5/1994 | Gunasingham | |
| 5,314,605 A | 5/1994 | Matthiessen | |
| 5,320,732 A | 6/1994 | Nankai et al. | |
| 5,382,346 A | 1/1995 | Uenoyama et al. | |
| 5,384,028 A | 1/1995 | Ito | |
| 5,385,846 A | 1/1995 | Kuhn et al. | |
| 5,393,399 A | 2/1995 | Van den Berg et al. | |
| 5,413,690 A | 5/1995 | Kost et al. | |
| 5,418,142 A | 5/1995 | Kiser et al. | |
| 5,427,912 A | 6/1995 | Brown et al. | |
| 5,434,055 A | 7/1995 | Jernigan | |
| 5,437,999 A | 8/1995 | Diebold et al. | |
| 5,460,924 A | 10/1995 | Buchanan et al. | |
| 5,508,171 A | 4/1996 | Walling et al. | |
| 5,509,410 A | 4/1996 | Hill et al. | |
| 5,518,590 A | 5/1996 | Fang | |
| 5,567,302 A | 10/1996 | Song et al. | |
| 5,602,040 A | 2/1997 | May et al. | |
| 5,628,890 A | 5/1997 | Carter et al. | |
| 5,645,709 A | 7/1997 | Birch et al. | |
| 5,656,731 A * | 8/1997 | Urdea | 530/391.1 |
| 5,707,584 A | 1/1998 | Terpstra et al. | |
| 5,776,324 A | 7/1998 | Usala | |
| 5,807,756 A * | 9/1998 | Bauman et al. | 436/524 |
| 5,842,787 A | 12/1998 | Kopf-Sill et al. | |
| 5,849,247 A | 12/1998 | Uzan et al. | |
| 5,922,615 A | 7/1999 | Nowakowski et al. | |
| 5,932,711 A | 8/1999 | Boles et al. | |
| 5,942,102 A | 8/1999 | Hodges et al. | |
| 5,951,492 A | 9/1999 | Douglas et al. | |
| 5,965,456 A | 10/1999 | Malmqvist | |
| 5,980,709 A | 11/1999 | Hodges et al. | |
| 5,997,617 A | 12/1999 | Czabala et al. | |
| 5,997,817 A | 12/1999 | Crismore et al. | |
| 6,054,039 A | 4/2000 | Shieh | |
| 6,103,033 A | 8/2000 | Say et al. | |
| 6,193,865 B1 | 2/2001 | Hodges et al. | |
| 6,214,205 B1 | 4/2001 | Willner et al. | |
| 6,218,134 B1 | 4/2001 | Yamauchi et al. | |
| 6,245,296 B1 | 6/2001 | Ligler et al. | |
| 6,325,973 B1 | 12/2001 | Leland et al. | |
| 6,405,066 B1 * | 6/2002 | Essenpreis et al. | 600/347 |
| 6,444,115 B1 | 9/2002 | Hodges et al. | |
| 6,495,823 B1 * | 12/2002 | Miller et al. | 250/286 |
| 6,602,702 B1 * | 8/2003 | McDevitt et al. | 435/288.7 |
| 6,615,856 B2 | 9/2003 | McNeely et al. | |
| 6,632,349 B1 | 10/2003 | Hodges et al. | |
| 6,638,415 B1 | 10/2003 | Hodges et al. | |
| 6,649,403 B1 * | 11/2003 | McDevitt et al. | 435/288.5 |
| 6,713,545 B2 | 3/2004 | Petiniot et al. | |
| 6,823,750 B2 | 11/2004 | Hodges et al. | |
| 7,184,894 B2 * | 2/2007 | Shimasaki et al. | 702/23 |
| 2002/0012943 A1 | 1/2002 | Fowlkes et al. | |

FOREIGN PATENT DOCUMENTS

| | | |
|---|---|---|
| DE | 3708031 | 12/1987 |
| EP | 0251915 A2 | 1/1988 |
| EP | 0255291 A2 | 2/1988 |
| EP | 0178647 A2 | 8/1988 |
| EP | 0278647 | 8/1988 |
| EP | 0345781 A2 | 12/1989 |
| EP | 0351516 A2 | 1/1990 |
| EP | 0400918 A1 | 12/1990 |
| EP | 0407800 A2 | 1/1991 |
| EP | 0415679 A2 | 3/1991 |
| EP | 0 422 708 | 4/1991 |
| EP | 0475692 A2 | 3/1992 |
| EP | 0479394 A2 | 4/1992 |
| EP | 483117 A2 * | 4/1992 |
| EP | 0 178 647 | 9/1993 |
| EP | 0560336 A1 | 9/1993 |
| EP | 0574134 A2 | 12/1993 |
| EP | 0 603 954 | 6/1994 |
| EP | 0 640 832 | 3/1995 |
| EP | 0741186 A2 | 11/1996 |
| EP | 0764469 A2 | 3/1997 |
| EP | 0 796 659 | 9/1997 |
| EP | 0 803 288 | 10/1997 |
| EP | 0964059 A2 | 12/1999 |
| EP | 1 347 302 A2 | 9/2003 |
| GB | 2201248 | 8/1988 |
| JP | 813496 | 5/1996 |
| JP | 9502799 | 3/1997 |
| JP | 10221341 | 8/1998 |
| JP | 2001059845 | 3/2001 |
| WO | WO 89/08713 | 9/1989 |
| WO | WO 92/15701 | 9/1992 |
| WO | WO 94/03496 | 2/1994 |
| WO | WO 95/16198 | 6/1995 |
| WO | WO 95/21934 | 8/1995 |
| WO | WO 95/28634 | 10/1995 |
| WO | WO 97/00441 A1 | 1/1997 |
| WO | WO 97/18464 A1 | 5/1997 |
| WO | WO 98/18465 A1 | 5/1997 |
| WO | WO 97/27474 A | 7/1997 |
| WO | WO 98/11426 | 3/1998 |

(56) References Cited

FOREIGN PATENT DOCUMENTS

| WO | WO 98/43073    | 10/1998 |
| WO | WO 98/43074    | 10/1998 |
| WO | WO 99/46585    | 9/1999  |
| WO | WO 99/49307    | 9/1999  |
| WO | WO 02/08762    | 1/2002  |
| WO | WO 02/08763 A1 | 1/2002  |

OTHER PUBLICATIONS

Gribnau CJ et al; Particle-labelled immunoassays: a review; Journal of Chromatography, Biomedical Applications 1986; 376: 175-189.
Kresl et al; Conversion of native oligometric to a modified monomeric form of human C-reactive protein; The International Journal of Biochemistry and Cell Biology 1998, 30: 1415-1426.
Minton 1981, Biopolymers, 20: 2093-2120.
Office Action translation for JP appl 2003-078391; Sep. 25, 2007.
European Search Report for EP 03251762 of Oct. 23, 2003.
Office Action for EP 01 961 64.6 issued Nov. 7, 2008.
English translation of second Office Action for JP appl. 2003-078391 issued Aug. 5, 2008.
Ronkainen-Matsuno, NJ, et al., "Electrochemical Immonoassay Moving into the Fast Lane" *Trends in Analytical Chemistry*, vol. 21, No. 4, 2002, pp. 213-225.
Canadian Intellectual Property Office, Office Action mailed in related Canadian Application No. 2,415,602 on Oct. 27, 2009, 3 pages.
Canadian Intellectual Property Office (CIPO), Examiner's Requisition, issued in corresponding Canadian Patent Application No. 2415602, mailed on Nov. 2, 2010, received Nov. 17, 2010, 3 pages.
Canadian Intellectual Property Office (CIPO), Notice of Allowance, issued in corresponding Canadian Patent Application No. 2415602, mailed on Jul. 28, 2011, received on Oct. 28, 2011, 1 page.
European Patent Office (EPO), Summons to Attend Oral Proceedings Pursuant to Rule 115 (1) EPC, issued in corresponding European Patent Application No. 01961641.6, mailed on Oct. 6, 2010, received Oct. 20, 2010, 4 pages.
European Patent Office (EPO), Decision to Refuse a European patent Application, issued in corresponding European Patent Application No. 01961641.6, mailed on Dec. 20, 2011, received Jan. 5, 2012, 30 pages.
Japanese Patent Office (JPO), Notification of Reasons for Refusal, issued in corresponding Japanese Patent Application No. 2002-514406, mailed on Oct. 5, 2010, received Nov. 10, 2010, 3 pages.
Japanese Patent Office (JPO), Notification of Reasons for Refusal, issued in corresponding Japanese Patent Application No. 2002-514406, mailed on Jun. 7, 2011, received Jul. 7, 2011, 2 pages.
Japanese Patent Office (JPO), Decision for Registration, issued in corresponding Japanese Patent Application No. 2002-514406, mailed on Sep. 27, 2011, received Oct. 3, 2011, 1 page.
US 5,883,400, 1/1999, Drummond et al. (withdrawn).
Abstract for JP 6310746 A; Miyahara et al.

* cited by examiner

IMMUNOSENSOR

This application is a continuation of application Ser. No. 09/616,433, filed Jul. 14, 2000 now abandoned, which is incorporated herein by reference in its entirety and to which we claim priority.

FIELD OF THE INVENTION

The present invention relates to a device and method for performing immunoassays. The device comprises a disposable immunosensor.

BACKGROUND OF THE INVENTION

Biomedical sensors are used to report the presence and/or concentration of a wide variety of analytes. When the analyte is a protein, then the sensing element used is usually an antibody since the interaction of the antibody with the protein (antigen) is very specific. Such immunoassays usually fall into two categories: a "yes/no answer" obtained, e.g., by simple visual detection, or a concentration of the antigen determined by a quantitative method. Most of the quantitative methods involve expensive pieces of equipment such as scintillation counters (for monitoring radioactivity), spectrophotometers, spectrofluorimeters (see, e.g., U.S. Pat. No. 5,156,972), surface plasmon resonance instruments (see, e.g., U.S. Pat. No. 5,965,456), and the like. It would therefore be advantageous to develop a quantitative immunoassay that is both inexpensive and simple enough to use to be suitable for home or field use.

Conventional immunoassays are classified into two categories: competition assay and sandwich assay. In a competition assay, the antigen in the test sample is mixed with an antigen-probe complex and the mixture then competes for binding to the antibody. The probe may be an enzyme, a fluorophore or a chromophore. Secondly, in a sandwich immunoassay, the antigen in the test sample binds to the antibody and then a second antibody-probe complex binds to the antigen. In these prior art assay methods, one or more washing steps are usually required. The washing steps introduce complexity into the assay procedure and can generate biohazardous liquid waste. It would therefore be advantageous to develop a device for performing an immunoassay that does not require any washing steps. Of necessity, such a device would be designed to be a single use disposable device.

SUMMARY OF THE INVENTION

This invention describes a quantitative, inexpensive, disposable immunosensor that requires no wash steps and thus generates no liquid waste. Moreover, in preferred embodiments of the sensor, no timing steps are required of the user, and the sensor can be readily adapted to antigen-antibody interactions over a wide kinetic range.

In one embodiment of the present invention, a disposable device is provided for use in detecting a target antigen in a fluid sample having a pH, the device including a reaction chamber having an internal surface, a proximal end, and a distal end; an immobilized antibody fixed within the reaction chamber, the antibody being capable of binding to the target antigen; a reporter complex present within the reaction chamber, the complex including a probe, the reporter complex being capable of mixing with the sample; a detection chamber having a wall, an internal surface, a distal end and a proximal end; a sample ingress at the distal end of the reaction chamber, and a sample passageway between the distal end of the reaction chamber and the proximal end of the detection chamber.

In one aspect of this embodiment, an agent contained within the reaction chamber and capable of preventing non-specific binding of proteins to the reaction chamber internal surface is included. The agent may be selected from the group consisting of a surfactant and a blocking protein, for example, bovine serum albumin.

In another aspect of this embodiment, the reporter complex further includes a second antigen capable of competing with the target antigen for binding to the immobilized antibody, or a second antibody capable of binding to the target antigen.

In another aspect of this embodiment, the probe is selected from the group consisting of chromophores and fluorophores. The probe may include an enzyme, such as glucose oxidase or glucose dehydrogenase. An enzyme substrate may also be included, for example, an oxidizable substrate such as galactose, acetic acid, or glucose.

In another aspect of this embodiment, the detection chamber further includes a mediator. The mediator may include dichlorophenolindophenol, complexes between transition metals and nitrogen-containing heteroatomic species, or ferricyanide.

In another aspect of this embodiment, the device further includes a buffer capable of adjusting the pH of the sample, such as one including phosphate or citrate.

In another aspect of this embodiment, the immobilized antibody and/or the reporter complex is supported on a reaction chamber interior surface. The reporter complex may be separated from the immobilized antibody by less than about 1 millimeter.

In another aspect of this embodiment, the device further includes a stabilizer that stabilizes one or more of the antigen, the enzyme, and the antibody.

In another aspect of this embodiment, the enzyme substrate is supported on a detection chamber interior surface.

In another aspect of this embodiment, the device further includes a support material. The support material may be contained within the detection chamber, and one or more substances such as an enzyme substrate, a mediator, and a buffer may be supported on or contained with the support material. The support material may also be contained within the reaction chamber, and one or more substances such as the immobilized antibody, the reporter complex, and an agent capable of preventing non-specific binding of proteins to the reaction chamber internal surface may be supported on or contained within the support material. The support material may include a mesh or fibrous filling material including a polymer selected from the group consisting of polyolefin, polyester, nylon, cellulose, polystyrene, polycarbonate, polysulfone, and mixtures thereof; a porous material such as a macroporous membrane including a polymeric material selected from the group consisting of polysulfone, polyvinylidene difluoride, nylon, cellulose acetate, polymethacrylate, polyacrylate, and mixtures thereof; or a sintered powder.

In another aspect of this embodiment, the detection chamber includes at least two electrodes. The electrodes may include a material selected from the group consisting of palladium, platinum, gold, iridium, carbon, carbon mixed with binder, indium oxide, tin oxide, and mixtures thereof.

In another aspect of this embodiment, the detection chamber wall is transparent to a radiation emitted or absorbed by the probe, the radiation being indicative of the presence or absence of the reporter complex in the detection chamber.

In another aspect of this embodiment, a detector capable of detecting a condition wherein the reaction chamber is substantially filled is included. A piercing means capable of forming a detection chamber vent in the distal end of the detection chamber may also be included. A reaction chamber vent at the distal end of the reaction chamber may be included as well.

In a second embodiment of the present invention, a method of manufacture of a disposable device for use in detecting a target antigen in a fluid sample having a pH is provided, the method including the steps of forming a first aperture extending through a first sheet of material having a proximal end and a distal end, the first aperture defining a reaction chamber side wall, a detection chamber side wall and a first sample passageway between the reaction chamber distal end and the detection chamber proximal end; mounting a first layer toga first side of the first sheet and extending over the aperture to define a first reaction chamber end wall and a first detection chamber end wall; mounting a second layer to a second side of the first sheet and extending over the aperture to define a second reaction chamber end wall and a second detection chamber end wall in substantial overlying registration with the first layer, whereby the sheet and layers form a strip having a plurality of exterior surfaces; forming a second passageway extending through an exterior surface of the strip and into the reaction chamber at the reaction chamber distal end, the second passageway defining a reaction chamber vent; forming a third passageway extending through the an exterior surface of the strip and into the reaction chamber at the reaction chamber proximal end, the third passageway defining a sample ingress; immobilizing an antibody within the reaction chamber; and placing a reporter complex in the reaction chamber, the complex including a probe.

In one aspect of this embodiment, the aperture extends through the proximal end of the first sheet to form the third passageway.

In another aspect of this embodiment, the first sheet, the first layer and the second layer include an electrically resistive material, the first layer includes a first electrode wherein the first electrode faces the first side of the first sheet, and the second layer includes a second electrode wherein the second electrode faces the second side of the sheet. At least one of the electrodes may include a material selected from the group consisting of palladium, platinum, gold, iridium, carbon, carbon mixed with binder, indium oxide, tin oxide, and mixtures thereof. The first electrode may substantially cover the first detection chamber end wall and the second electrode substantially covers the second detection chamber end wall. At least one of the electrodes may be a sputter coated metal deposit. The second electrode may be mounted in opposing relationship a distance of less than about 500 microns from the first electrode; less than about 150 microns from the first electrode; or less than about 150 microns and greater than about 50 microns from the first electrode.

In another aspect of this embodiment, the layers are adhered to the sheet, for example, by an adhesive such as a heat activated adhesive, pressure sensitive adhesive, heat cured adhesive, chemically cured adhesive, hot melt adhesive, and hot flow adhesive. At least the sheet, or one of the layers may include a polymeric material such as polyester, polystyrene, polycarbonate, polyolefin, and mixtures thereof, or polyethylene terephthalate. At least one of the layers may be transparent to a wavelength of radiation including infrared radiation, visible light, and ultraviolet radiation.

In another aspect of this embodiment, the method further includes providing an enzyme substrate and a mediator, wherein the enzyme substrate and the mediator are contained within the detection chamber, wherein the probe is an enzyme, and wherein the mediator is capable of mediating a reaction between the enzyme and the electrode, to indicate the occurrence of an electrochemical reaction.

In another aspect of this embodiment, the method further includes the step of providing a buffer, wherein the buffer is capable of adjusting the pH of the sample.

In a third embodiment of the present invention, a method of manufacture of a disposable device for use in detecting a target antigen in a fluid sample having a pH is provided, the method including forming a first aperture extending through a first sheet of electrically resistive material having a proximal end and a distal end, the first aperture having a first aperture reaction chamber part and a first aperture detection chamber part and defining a first portion of a reaction chamber side wall, a detection chamber side wall and a sample passageway between the reaction chamber distal end and the detection chamber proximal end; forming a second aperture extending through a second sheet of electrically resistive material having a proximal end and a distal end, the second aperture defining a second portion of the reaction chamber side wall; forming a third aperture extending through a third sheet of electrically resistive material having a proximal end and a distal end, the third aperture defining a third portion of the reaction chamber side wall; mounting a first side of the second sheet to a first side of the first sheet, the second sheet extending over the first aperture detection chamber part whereby to define a first detection chamber end wall, the second portion of the reaction chamber side wall in substantial registration with the first portion of the reaction chamber side wall; mounting a first side of the third sheet to a second side of the first sheet, the third sheet extending over the first aperture detection chamber part whereby to define a second detection chamber end wall, the third portion of the reaction chamber side wall in substantial registration with the first portion of the reaction chamber side wall; mounting a first layer to a second side of the second sheet and extending over the second aperture to define a first reaction chamber end wall; mounting a second layer to a second side of the third sheet and extending over the third aperture to define a second reaction chamber end wall in substantial overlying registration with the first thin layer, whereby the sheets and layers form a strip having a plurality of exterior surfaces; forming a second passageway extending through the outside of the strip and into the reaction chamber at the reaction chamber distal end, the second passageway defining a reaction chamber vent; forming a third passageway extending through the outside of the strip and into the reaction chamber at the reaction chamber proximal end, the third passageway defining a sample ingress; immobilizing an antibody within the reaction chamber; and placing a reporter complex in the reaction chamber, the reporter complex including a probe.

In a fourth embodiment of the present invention, a method for determining a presence or an absence of a target antigen in a fluid sample is provided, the method including providing a disposable device including a reaction chamber having an internal surface, a proximal end, and a distal end, an immobilized antibody fixed within the reaction chamber, the antibody being capable of binding to the target antigen, a reporter complex present within the reaction chamber, the complex including a probe, the reporter complex being capable of mixing with the sample, a detection chamber having a wall, an internal surface, a distal end and a proximal end, a sample ingress at the distal end of the reaction chamber, and a sample passageway between the distal end of the reaction chamber and the proximal end of the detection chamber, wherein the reporter complex further includes a second antigen capable of competing with the target antigen for binding to the immobilized antibody; contacting a fluid sample with the sample ingress; substantially filling the reaction chamber with the fluid sample by allowing the sample to flow from the sample ingress toward the reaction chamber; allowing a predetermined time to lapse, the time being sufficient for substantially all reporter complex to bind to the immobilized antibody in the absence of antigen in the sample; substantially filling the detection chamber with the fluid sample by allowing the sample to flow from the reaction chamber through the sample passageway toward the detection chamber; detecting a presence or an absence of the antigen-probe complex within the detection chamber, the presence or absence of the antigen-probe complex being indicative of a presence or an absence of the antigen in the sample.

In one aspect of this embodiment, then method further includes piercing the wall of the detection chamber so as to form a detection chamber vent at the distal end of the detection chamber, the piercing step immediately following the lapse of the predetermined time.

In a fifth embodiment of the present invention, a method of manufacture of a disposable device for use in detecting a target antigen in a fluid sample having a pH is provided, the device having a plurality of exterior surfaces, the method including forming a first aperture extending through a first sheet of electrically resistive material, the first aperture having a detection chamber part and defining a detection chamber side wall, the detection chamber having a proximal end and a distal end; mounting a first layer to a first side of the first sheet and extending over the aperture to define a first detection chamber end wall; mounting a second layer to a second side of the first sheet and extending over the aperture to define a second detection chamber end wall in substantial overlying registration with the first layer, whereby the sheet and layers form a strip; forming a second aperture extending through the strip, the strip having a proximal end and a distal end, the second aperture having a reaction chamber part, the reaction chamber having a distal end and a proximal end, and the second aperture defining a reaction chamber side wall and a sample passageway between the reaction chamber distal end and the detection chamber proximal end; mounting a first side of a third layer to a first side of the strip, the third extending over the second aperture reaction chamber part to define a first reaction chamber end wall; mounting a first side of a fourth layer to a second side of the strip, the fourth layer extending over the second aperture reaction chamber part whereby to define a second reaction chamber end wall in substantial registration with the first reaction chamber end wall; forming a third aperture extending through a surface of the device and into the reaction chamber at the reaction chamber distal end, the third aperture defining a reaction chamber vent; forming a fourth aperture extending through a surface of the device and into the reaction chamber at the reaction chamber proximal end, the fourth aperture defining a sample ingress; immobilizing an antibody within the reaction chamber, and placing a reporter complex in the reaction chamber, the reporter complex including a probe.

In one aspect of this embodiment, the first sheet, the first layer and the second layer include an electrically resistive material, the first layer includes a first electrode wherein the first electrode faces the first side of the first sheet, and the second layer includes a second electrode wherein the second electrode faces the second side of the sheet.

DETAILED DESCRIPTION OF THE PREFERRED EMBODIMENTS

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Disclosed is a single step, no-wash immunosensor. The sensor is a single use, disposable device that utilizes two adjacent chambers, a reaction chamber and a detection chamber. In the reaction chamber, the antigen-antibody reactions take place and in the detection chamber the results of those reactions are detected and the presence or absence of antigen in the sample is inferred.

Any suitable detection method can be utilized. Suitable detection methods include, e.g., visual detection wherein the development of a color is observed, or spectroscopic detection wherein reflected or transmitted light is used to measure changes in light absorbance. In a preferred embodiment, the detection method is electrochemical wherein the electrical current or potential generated indirectly by the products of antigen/antibody reactions is measured.

Methods and devices for obtaining electrochemical measurements of fluid samples are discussed further in U.S. patent application Ser. No. 09/615,691, now U.S. Pat. No. 6,638,415, filed on Jul. 14, 2000, entitled "ANTIOXIDANT SENSOR," U.S. patent application Ser. No. 09/616,512, now U.S. Pat. No. 6,632,349 filed on Jul. 14, 2000, entitled "HEMOGLOBIN SENSOR," and U.S. patent application Ser. No. 09/616,556, filed on Jul. 14, 2000, now U.S. Pat. No. 6,445,115, entitled "ELECTROCHEMICAL METHOD FOR MEASURING CHEMICAL REACTION RATES," each of which is incorporated herein by reference in its entirety.

The timing of the various test stages, i.e., the reaction stage and the detection stage may be done manually. Alternatively, timing may be done automatically in response to a trigger signal generated when the reaction chamber is filled.

Figure 1:
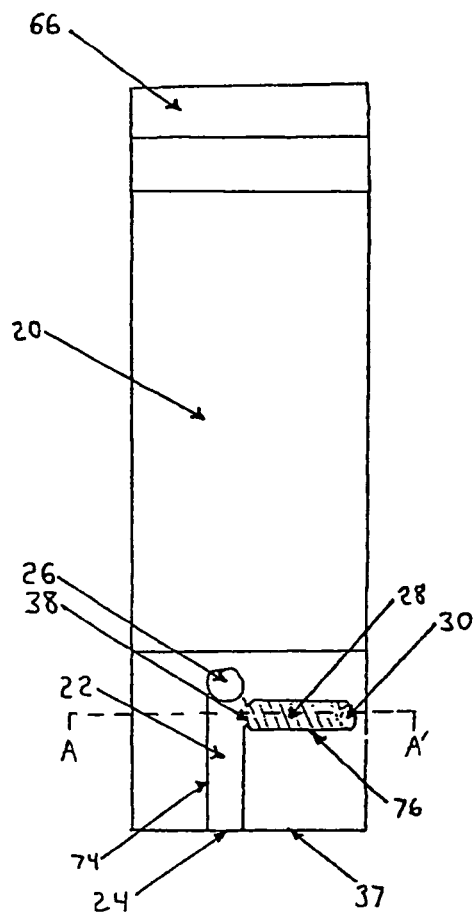
FIG. 1 shows a top view (not to scale) of an immunosensor incorporating an electrochemical cell.
Figure 2:
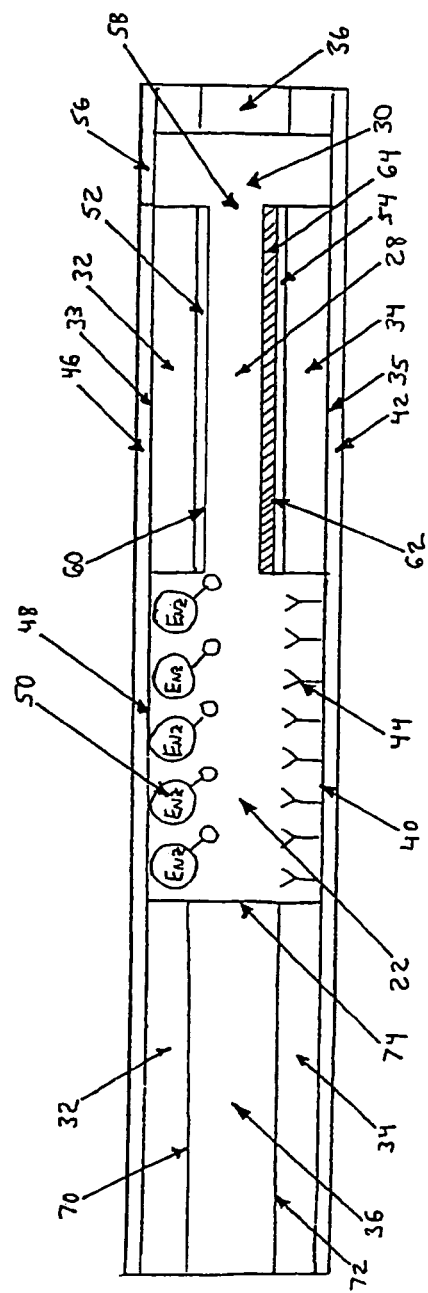
FIG. 2 shows a cross-sectional view (not to scale) along line A-A' of an embodiment of the immunosensor of FIG. 1.

An embodiment of the sensor suitable for use with electrochemical detection is illustrated in FIGS. 1 and 2. FIG. 1 is a top view of the sensor strip and FIG. 2 is a cross-sectional view, showing details of the reaction chamber and the detection chamber.

The Sensor

The immunosensors of the present invention may be prepared using well-known thin layer device fabrication techniques as are used in preparing electrochemical glucose sensing devices (see, e.g., U.S. Pat. No. 5,942,102, incorporated herein by reference in its entirety). Such techniques, with certain modifications, are also used to prepare immunosensors utilizing non-electrochemical detection methods.

In a preferred embodiment of the immunosensor, illustrated in FIGS. 1 and 2, the detection chamber 28 comprises an electrochemical cell. The reaction chamber 22 and detection chamber 28 are prepared by first forming an aperture extending through a sheet of electrically resistive material 36. The aperture is shaped such that it defines a sidewall of both the reaction chamber 22 and the detection chamber 28, as well as the sample passageway 38 between the two chambers 22 and 28. By extending the aperture from the proximal end 24 of the reaction chamber 22 through to the edge 37 of the sheet 36, the sample ingress 24 is also formed. In one embodiment, the thickness of the sheet 36 defines the entire height of the reaction chamber 22 and detection chamber 28, which are the same. In another embodiment, the height of the reaction chamber 22 is greater than that of the detection chamber 28. A reaction chamber 22 of greater height than the detection chamber 28 is prepared by layering multiple sheets 32, 34, and 36 together. Sheet 36 in the middle of the layer has an aperture defining the sidewalls 74 and 76 of both the reaction chamber 22 and detection chamber 28 as described above. The middle sheet 36 is then sandwiched between two or more additional sheets 32 and 34, the additional sheets 32 and 34 having an aperture defining the side wall 74 of the reaction chamber 22 only, the sheets 32 and 34 thereby defining end walls 60 and 62 of the detection chamber 28. In this embodiment, the end walls 60 and 62 of the detection chamber must also comprise thin electrodes 52 and 54, which may be prepared as described below.

After the sidewalls 74 and 76 of the reaction chamber 22 and detection chamber 28 are formed, a first thin electrode 52 is then mounted on one side 70 of the sheet of electrically resistive material 36, extending over the aperture forming the detection chamber 28 and forming an end wall 60. The first thin electrode 52 may be adhered to the sheet 36, e.g., by means of an adhesive. Suitable adhesives include, for example, heat activated adhesives, pressure sensitive adhesives, heat cured adhesives, chemically cured adhesives, hot melt adhesives, hot flow adhesives, and the like. The first thin electrode 52 is prepared by coating (e.g., by sputter coating) a sheet of electrically resistive material 32 with a suitable metal, for example, platinum, palladium, carbon, indium oxide; tin oxide, mixed indium/tin oxides, gold, silver, iridium, mixtures thereof, and the like. Materials suitable for use as thin electrodes 52 and 54 must be compatible with the reagents present in the sensor 20, i.e., they will not react chemically with reagents.

A second thin electrode 54 is then mounted on the opposite side of the sheet of electrically resistive material 36, also extending over the aperture forming the detection chamber 28, so as to form a second end wall 62. In a preferred embodiment, the thin electrodes 52 and 54 are mounted in opposing relationship at a distance of less than about 500 microns, more preferably less than 150 microns, and most preferably between 50 and 150 microns. If a sample ingress 24 has not already been formed, then one must be provided, e.g., by forming a notch in the edge 37 of the device 20 that intersects the proximal end of the reaction chamber 22.

The electrodes 52 and 54 are provided with connection means allowing the sensor 20 to be placed in a measuring circuit. At least one of the electrodes 52 or 54 in the cell is a sensing electrode, i.e., an electrode sensitive to the amount of reduced redox agent in the antioxidant case or oxidized redox agent in the oxidant case. In the case of a potentiometric sensor 20 wherein the potential of the sensing electrode 52 or 54 is indicative of the level of analyte present, a second electrode 54 or 52, acting as reference electrode is present which acts to provide a reference potential. In the case of an amperometric sensor 20 wherein the sensing electrode current is indicative of the level of analyte in the sample, at least one other electrode 54 or 52 is present which functions as a counter electrode to complete the electrical circuit. This second electrode 54 or 52 may also function as a reference electrode. Alternatively, a separate electrode (not shown) may perform the function of a reference electrode.

If the immunosensor 20 is operated as an electrochemical cell, then the sheets 32, 34, and 36 containing the apertures defining the reaction chamber 22 and/or detection chamber 28 should comprise electrically resistive materials. Suitable electrically resistive materials include, for example, polyesters, polystyrenes, polycarbonates, polyolefins, mixtures thereof, and the like. A preferred polyester is polyethylene terephthalate. If the immunosensor 20 is operated using a detection method other than an electrochemical detection method, then the materials need not be electrically resistive. However, the polymeric materials described above are preferred for use in constructing the immunosensors of a preferred embodiment because of their ease of processing, low cost, and lack of reactivity to reagents and samples. In the case of a detection method involving absorbance, transmission, or emission of light of a particular frequency, then the end walls 60 and/or 62, sheets 32, 34 and layers 46, 42 above the end walls of the detection chamber 28 should be transparent to that light frequency.

Reagents for use in the cell, e.g., immobilized antibody, enzyme-linked antigen, buffer, mediator, and the like, may be supported on the internal surfaces 40, 48, and/or sidewall 74 of the reaction chamber 22 or on the end walls 60, 62, and/or sidewall 76 of the detection chamber 28, on an independent support contained within chambers, within a matrix, or may be self supporting. If the reagents are to be supported on the chamber walls or electrodes 52 and 54, the chemicals may be applied by use of printing techniques well known in the art, e.g., ink jet printing, screen printing, lithography, and the like. In a preferred embodiment, a solution containing the reagent is applied to a surface within a chamber and allowed to dry.

Rather than immobilize or dry the antibodies 44, the enzyme-linked antigen 50, or other chemicals onto the internal surfaces 40, 48, onto the end walls 60, 62, or onto the sidewalls 74, and/or 76 of the reaction chamber 22 or detection chamber 28, it may be advantageous to support them on or contain them within one or more independent supports which are then placed into a chamber. Suitable independent supports include, but are not limited to, mesh materials, nonwoven sheet materials, fibrous filling materials, macroporous membranes, or sintered powders. The advantages of independent supports include an increased surface area, thus allowing more antibody and enzyme-linked antigen to be included in the reaction chamber, if desired. In such an embodiment, the antibody is immobilized on one piece of porous material and placed in the first reaction chamber and the enzyme-linked antigen is dried onto a second piece of porous material, which is then placed into the reaction chamber. Alternatively, either the antibody or the enzyme-linked antigen are incorporated onto the porous material and the other component supported on the reaction chamber wall as described above. In yet another embodiment, the walls of the reaction chamber themselves are porous, with the antibody and/or probe enzyme-linked antigen incorporated in them. In this embodiment, the liquid is able to wick into the porous wall, but not leak out of the defined area. This is accomplished by using a macroporous membrane to form the reaction chamber wall and compressing the membrane around the reaction chamber to prevent leakage of sample out of the desired area.

Suitable independent supports such as mesh materials, nonwoven sheet materials, and fibrous fill materials include, polyolefins, polyesters, nylons, cellulose, polystyrenes, polycarbonates, polysulfones, mixtures thereof, and the like. Suitable macroporous membranes may be prepared from polymeric materials including polysulfones, polyvinylidene difluorides, nylons, cellulose acetates, polymethacrylates, polyacrylates, mixtures thereof, and the like.

The protein or antibody may be contained within a matrix, e.g., polyvinyl acetate. By varying the solubility characteristics of the matrix in the sample, controlled release of the protein or antibody into the sample may be achieved.

In all cases, the materials used within the sensor are in a form amenable to mass production, and the cells themselves are designed to be able to be used for a single experiment then disposed of.

A preferred embodiment of an immunosensor that is fabricated as described above is illustrated in FIGS. 1 and 2. In this preferred embodiment, the sheets of electrically resistive material 32 and 34 are coated with electrically conductive material that forms the thin electrodes 52 and 54. The electrically conductive material is coated on the surface of end walls 60 or 62 facing the detection chamber 28 and an adhesive layer (not shown) is coated on the surface 33 or 35 facing layer 42 or 46, respectively.

Using the Sensor to Determine the Presence or Absence of an Antigen

In a preferred embodiment, the sensor 20 is an electrochemical cell utilizing an enzyme, e.g., glucose oxidase or glucose dehydrogenase, as the probe, as illustrated in FIG. 1, a top view of such a sensor 20, and FIG. 2, a cross section of the sensor through line A-A'. The presence or absence of an analyte is inferred in this embodiment as follows.

The user first introduces sample into the reaction chamber 22 of the sensor 20 through the sample ingress 24. The sample is drawn into the reaction chamber 22 under the influence of capillary or wicking action. During filling the reaction chamber vent 26 is open to the atmosphere, thus allowing air displaced by the sample to escape. Sample will be drawn into the reaction chamber 22 until it is filled up to the reaction chamber vent 26, whereupon filling will stop. The volume of the reaction chamber 22 is chosen so as to be at least equal to and preferably larger than the volume of the detection chamber 28.

The dashed circle in FIG. 1 denotes an aperture 30 piercing sheets 32, 34, and 36 but not layers 42 and 46, the aperture in sheet 34 opening into the detection chamber 28. Since layers 42 and 46 are not pierced initially, the only opening to the atmosphere of the detection chamber 28 is the sample passageway 38 opening into the reaction chamber 22. Thus, when the reaction chamber 22 fills with sample, it blocks the sample passageway 38 to the detection chamber 28. This traps air in the detection chamber 28 and substantially prevents it from filling with sample. A small amount of sample will enter the detection chamber 28 during the time between when the sample first contacts the opening of the sample passageway 38 to the detection chamber 28 and when it contacts the far side of the opening of the sample passageway 38. However, once the sample has wet totally across the opening to the detection chamber 28, no more filling of the detection chamber 28 will take place.

The internal surface 40 of the layer 42, which forms the base of the reaction chamber 22, is coated with antibodies 44 to the antigen to be detected. The antibodies 44 are adsorbed or otherwise immobilized on the surface 40 of the layer 42 such that they are not removed from the layer 42 during a test. Optionally, after application of the antibodies 44 to the internal surface 40 of the layer 42, an agent designed to prevent non-specific binding of proteins to this surface can be applied (not shown). An example of such an agent well known in the art is bovine serum albumin (BSA). A nonionic surfactant may also be used as such an agent, e.g., Triton X100™ manufactured by Rohm & Haas of Philadelphia, Pa., or Tween™ manufactured by ICI Americas of Wilmington, Del. The nonionic surfactant selected must not denature proteins. The antibodies 44 coating the internal surface 40 of the layer 42 are in the dry state when ready to be used in a test.

Another layer 46 defines the internal surface 48 of the reaction chamber 22. On the internal surface 48 of the layer 46 are coated the enzyme-linked antigens 50 to be detected. Examples of suitable enzymes include, but are not limited to, glucose oxidase and glucose dehydrogenase. The enzyme-linked antigen 50 is dried onto the internal surface 48 of the layer 46 in such a way that it can be liberated into the sample when the internal surface 48 is wet by the sample. The internal surface 48 of the layer 46 and the method for coating on the enzyme-linked antigen 50 are therefore chosen such that only a weak bond between the enzyme-linked antigen 50 and the internal surface 48 of the layer 46 exists. The rate of dissolution of the enzyme-linked antigen 50 from the internal surface 48 is chosen such that little dissolution has occurred during the time taken for the sample to fill the reaction chamber 22. In this manner, the enzyme-linked antigen 50 will be evenly distributed throughout the area of the reaction chamber 22 after filling.

The relative amounts of enzyme-linked antigen 50 and antibody 44 are chosen such that there is a slight excess of antibody 44 over enzyme-linked antigen 50. In this context, a slight excess is defined to be such that the excess is small when compared to the number of antigen molecules to be detected in the sample.

Thus, when sample fills the reaction chamber 22 the enzyme-linked antigen 50 enters and mixes with the sample. Sufficient time is then allowed for the enzyme-linked antigen 50 to come into contact with the antibodies 44. Since there is excess of antibodies 44, if no antigen is present in the sample then substantially all of the enzyme-linked antigen 50 will bind to the antibodies 44 and so be effectively immobilized. If antigen is present in the sample, the antigen, being smaller than the enzyme-linked antigen 50 and already present throughout the volume of the sample, will contact and bind to the antibodies 44 before the enzyme-linked antigen 50 contacts the antibodies 44. The antibodies 44 will therefore be blocked and prevented from binding to the enzyme-linked antigen 50. So if antigen is initially present in the sample then, at the end of the reaction step, enzyme-linked antigen 50 will remain mobile in the sample. If no antigen is initially present in the sample, the enzyme-linked antigen 50 will be immobilized to the antibodies 44 on the internal surface 48 of layer 46 at the end of the reaction step.

The end of the reaction step is a predetermined time after the sample is introduced into the reaction chamber 22. The predetermined time is set such that there is sufficient time for substantially all of the enzyme-linked antigen 50 to bind to the antibodies 44 under the test conditions when no antigen is initially present in the sample.

The time that the sample is introduced into the reaction chamber 22 can be indicated by the user, for example, by depressing a button on a meter connected to the sensor 20. This action is used to trigger a timing device. In the case of visual detection, no meter device is necessary. In such an embodiment, the user manually times the reaction period.

In the case where electrochemical detection is used to detect the result of the antibody/antigen reactions, the indication that sample has been introduced into the reaction chamber 22 can be automated. As described above, when sample fills the reaction chamber 22, a small portion of the detection chamber 28 at its opening into the reaction chamber 22 will be wet by sample. If electrochemical detection is employed then at least two thin electrodes 52 and 54 will be present in the detection chamber 28. If the thin electrodes 52 and 54 are placed in the detection chamber 28, such that at least a portion of each thin electrode 52 and 54 is contacted by the sample during the filling of the reaction chamber 22, the presence of the sample will bridge the thin electrodes 52 and 54 and create an electrical signal which can be used to trigger the timing device.

A predetermined time after the timing device has been triggered, either by the user or automatically, the antibody/antigen reaction phase of the test is deemed to be completed. When the antibody/antigen phase of the test is completed, the vent 56 to the atmosphere is opened. For example, a solenoid activated needle in the meter may be used to pierce layer 42 or layer 46 or both layers 42 and 46, thus opening the distal end 58 of the detection chamber 28 to the atmosphere. The piercing can be automatically performed by the meter, as in the example above, or manually by the user in the case of visual detection wherein no meter may be used, e.g., the user inserts a needle through the layers 42 and 46, thereby forming the vent 56.

The opening of the vent 56 to the atmosphere allows the air trapped in the detection chamber 28 escape, thereby allowing the detection chamber 28 to be filled with reacted sample from the reaction chamber 22. The reacted sample will be drawn into the detection chamber 28 due to increased capillary force in the detection chamber 28 compared to that present in the reaction chamber 22. In a preferred embodiment, the increased capillary force is provided by suitably coating the surfaces of end walls 60 and 62 of the detection chamber 28 or, more preferably, by choosing the capillary distance for the detection chamber 28 to be smaller than that of the reaction chamber 22. In this embodiment, the capillary distance is defined to be the smallest dimension of the chamber.

Optionally disposed in the detection chamber 28 are dried reagents 64 comprising an enzyme substrate and a mediator, capable of reacting with the enzyme part of the enzyme-linked antigen 50 to produce a detectable signal. The enzyme substrate and mediator, if present, are to be of sufficient amount such that the rate of reaction of any enzyme present with the enzyme substrate is determined by the amount of enzyme present. For instance, if the enzyme were glucose oxidase or glucose dehydrogenase, a suitable enzyme mediator and glucose (if not already present in the sample) would be disposed into the detection chamber 28. Buffer may also be included to help adjust the pH of the sample in the detection chamber 28 if necessary. In an embodiment wherein an electrochemical detection system is used, ferricyanide is a suitable mediator. Other suitable mediators include dichlorophenolindophenol and complexes between transition metals and nitrogen-containing heteroatomic species. The glucose, mediator and buffer reagents are present in sufficient quantities such that the rate of reaction of the enzyme with the enzyme substrate is limited by the concentration of the enzyme present.

When the detection chamber 28 is filled, the dried reagents 64 dissolve into the sample. The enzyme component of the enzyme-linked antigen 50 reacts with the glucose and the mediator to produce reduced mediator. This reduced mediator is electrochemically oxidized at an electrode 52 or 54 acting as an anode in the detection chamber 28 to produce an electrical current. In one embodiment, the rate of change of this current with time is used as an indicator of the presence and amount of enzyme that is present in the reacted sample. If the rate of change of current is less than a predetermined threshold value, then it is indicative of no significant amount of enzyme-linked antigen 50 present in the reacted sample, indicating the lack of antigen present in the original sample. If the rate of change of current is higher than the threshold rate, it indicates that enzyme-linked antigen 50 is present in the reacted sample, and thus antigen is also present in the sample initially. In one embodiment, the rate of change of the current is used to give a measure of the relative amount of antigen initially present in the sample.

In a preferred embodiment of the electrochemical detection system, the thin electrodes 52 and 54 in the detection chamber 28 are formed as electrically conductive layers coated onto the surfaces of end walls 60 and 62, e.g., by sputtering as disclosed in WO97/18464. These conductive layers are of materials that do not react chemically with reagent present and are useful as electrodes 52 and 54 at the potential of choice. Examples of suitable materials include, but are not limited to, palladium, platinum, gold, iridium, carbon, carbon mixed with a binder, indium oxide, tin oxide, and mixed oxides of indium and tin.

In this embodiment, an inert, electrically insulating sheet 36 separates the electrode-bearing sheets 32 and 34. Preferably, insulating sheet 36 functions to keep sheets 32 and 34 at a predetermined separation. Provided this separation is small enough, e.g., less than 500 micron and more preferably from 50 to 150 microns, the current flowing between the electrodes 52 and 54 will be directly proportional to the concentration of reduced mediator after a suitably short time relative to the detection time employed. In this embodiment, the rate of current rise is directly related to the rate of the enzyme reaction and therefore the amount of enzyme present.

In FIG. 1, a connection end 66 is shown. The thin electrodes 52 and 54 (not shown) in the detection chamber 28 can be placed in electrical connection with a meter (not shown) through the connection end 66. The connection means (not shown) connects the meter (not shown) to the thin electrodes 52 and 54 in the detection chamber 28 via conducting tracks (not shown). In the preferred embodiment illustrated in FIG. 2, the conducting tracks are extensions of the electrically conductive material that form the thin electrodes 52 and 54 and are coated onto the internal surfaces of sheets 32 and 34. The meter in connection with the connection end 66 (not shown) is capable of applying a potential between the thin electrodes 52 and 54 in the detection chamber 28, analyzing the electrical signals generated, displaying a response and optionally storing the response in memory.

In other embodiments utilizing electrochemical detection, stripes of conducting material on one or both internal faces of the detection chamber are used, with the provision that at least two electrodes are present, i.e., a sensing electrode and a counter/reference electrode. Optionally, a third electrode, serving as a separate reference electrode, is included.

In the case of an embodiment wherein visual detection or reflectance spectroscopy is the detection method used, at least the sheet 32 and layer 46 or sheet 34 and layer 42 are transparent to the wavelength of radiation that is to be observed. In the case of visual detection, a simple color change in the detection chamber 28 is observed. In the case of reflectance spectroscopy, detection radiation is shone through sheet 32 and layer 46 or sheet 34 and layer 42, and radiation reflected from the solution in the detection chamber 28 is analyzed. In the case of transmission spectroscopy used as the detection method, at least sheet 32 and layer 46, or sheet 34 and layer 42, are transparent to radiation at the wavelength of choice. Radiation is shone through the sample in the detection chamber 28 and the attenuation of the beam is measured.

In a preferred embodiment of a method of constructing the sensor, sheet 36 comprises a substrate with a layer of adhesive (not shown) coated on its upper surface 70 and lower surface 72. Examples of materials suitable for the substrate of sheet 36 include polyester, polystyrene, polycarbonate, polyolefins, and, preferably, polyethylene terephthalate. Examples of suitable adhesives are pressure sensitive adhesives, heat and chemically curing adhesives and hot melt and hot flow adhesives.

Use of Melitten as a Probe

Conventional ELISAs link an antigen to an enzyme. However, it is also possible to link the antigen to melittin, a polypeptide found in bee venom. In this embodiment, a probe-linked antigen comprising an antigen-melittin complex can bee dried on a wall of the reaction chamber, as described above. The detection chamber can contain a mediator comprising ferrocyanide in liposomes or lipid vesicles. If the antigen-melittin complex reaches the liposomes, they will burst and release the ferrocyanide. This leads to a rapid amplification of the signal, i.e., a small amount of free antigen competes with the antigen-melittin complex for binding sites on the antibodies and results in a large concentration of ferrocyanide.

Use of Horse Radish Peroxidase and Alkaline Phosphatase in Electrochemical Assays Conventional ELISAs use horse radish peroxidase (HRP) or alkaline phosphatase (AP) as the enzymes in a calorimetric assay. However, substrates have been developed which allow both these enzymes to be used in an electrochemical assay. In this embodiment, AP can be used with p-aminophenyl phosphate and HRP can be used with tetrathiafulvalene.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An electrochemical device for use in detecting a target antigen in a fluid sample, the device comprising:
   a reaction chamber including
      a) an internal surface, a proximal end, and a distal end,
      b) an immobilized antibody that can bind to the target antigen, said antibody being immobilized to an internal surface of the reaction chamber or said antibody being immobilized onto a support placed within the reaction chamber, and
      c) a reporter comprising an enzyme probe and an antigen configured for binding with the immobilized antibody;
   a detection chamber including
      a) an internal surface, a distal end, and a proximal end,
      b) electrodes for detecting an electrochemical reaction in the detection chamber, and
      c) a zone having a wall at the distal end of the detection chamber, wherein the wall is capable of being pierced to form a vent; and
   a sample passageway between the distal end of the reaction chamber and the proximal end of the detection chamber, the detection chamber trapping air when the fluid sample enters the sample passageway, preventing ingress of the fluid sample into the detection chamber;
   wherein the device is adapted to move the sample from the reaction chamber to the detection chamber via capillary action upon opening the vent by piercing the wall of the zone in the detection chamber to release trapped air, and wherein the presence of a target antigen in the fluid sample results in a measurable change in an electrochemical reaction in the detection chamber.

2. The device of claim 1, wherein the reaction chamber includes an excess of antibody.

3. The device of claim 1, wherein the enzyme comprises glucose oxidase.

4. The device of claim 1, wherein the enzyme comprises glucose dehydrogenase.

5. The device of claim 1, wherein the detection chamber further comprises an enzyme substrate.

6. The device of claim 5, wherein the enzyme substrate is an oxidizable enzyme substrate.

7. The device of claim 6, wherein the oxidizable enzyme substrate is selected from the group consisting of galactose and acetic acid.

8. The device of claim 6, wherein the oxidizable enzyme substrate comprises glucose.

9. The device of claim 1, wherein the detection chamber further comprises a mediator.

10. The device of claim 9, wherein the mediator is selected from the group consisting of dichlorophenolindophenol and complexes between the transition metals and nitrogen-containing heteroatomic species.

11. The device of claim 9, wherein the mediator comprises ferricyanide.

12. The device of claim 1, wherein the detection chamber further comprises a buffer for adjusting the pH of a sample.

13. The device of claim 12, wherein the buffer comprises phosphate.

14. The device of claim 12, wherein the buffer comprises citrate.

15. The device of claim 1, further comprising an agent contained within the reaction chamber, the agent adapted to prevent non-specific binding of proteins to the reaction chamber internal surface.

16. The device of claim 15, wherein the agent is selected from the group consisting of a surfactant and a blocking protein.

17. The device of claim 15, wherein the agent is bovine serum albumin.

18. The device of claim 1, wherein the reporter is spaced from the immobilized antibody by less than about 1 millimeter.

19. The device of claim 1, wherein the device further comprises a support material.

20. The device of claim 19, wherein the support material is positioned within the detection chamber and wherein a first substance selected from the group consisting of an enzyme substrate, a mediator, a buffer, and combinations thereof is supported on or contained within the support material.

21. The device of claim 19, wherein the support material is positioned within the reaction chamber and wherein a second substance selected from the group consisting of the immobilized antibody, the reporter, and an agent adapted to prevent non-specific binding of proteins to the reaction chamber internal surface is supported on or contained within the support material.

22. The device of claim 19, wherein the support material comprises a mesh material.

23. The device of claim 19, wherein the support material comprises a fibrous filling material.

24. The device of claim 19, wherein the support material comprises a porous material.

25. The device of claim 24, wherein the porous material comprises sintered powder.

26. The device of claim 24, wherein the porous material comprises a macroporous membrane.

27. The device of claim 1, further comprising a detector adapted to detect a condition wherein the reaction chamber is substantially filled.

28. The device of claim 1, further comprising a reaction chamber vent at the distal end of the reaction chamber.

\* \* \* \* \*